United States Patent [19]

Burri

[11] 4,343,944
[45] Aug. 10, 1982

[54] INDOLINOSPIROPYRANE COMPOUNDS

[75] Inventor: Peter Burri, Reinach, Switzerland

[73] Assignee: Ciba-Geigy Corporation, Ardsley, N.Y.

[21] Appl. No.: 213,298

[22] Filed: Dec. 5, 1980

Related U.S. Application Data

[62] Division of Ser. No. 109,741, Jan. 4, 1980, which is a division of Ser. No. 761,042, Jan. 21, 1977, Pat. No. 4,210,591.

[30] Foreign Application Priority Data

Jan. 30, 1976 [CH] Switzerland .......................... 1175/76
Sep. 7, 1976 [CH] Switzerland ........................ 11326/76

[51] Int. Cl.³ .................. C07D 213/04; C07D 209/04
[52] U.S. Cl. ............................. 546/15; 260/326.11 S;
548/336; 548/374; 548/147; 548/207; 260/315;
427/151; 282/27.5
[58] Field of Search ................. 260/326.11 S; 546/15

[56] References Cited

U.S. PATENT DOCUMENTS

3,212,898 10/1965 Cerreta ...................... 260/326.11 S
3,299,079 1/1967 Taylor ................................... 546/15
3,999,989 12/1976 Ono et al. ................... 260/326.11 S

FOREIGN PATENT DOCUMENTS

2516383 10/1975 Fed. Rep. of Germany ................... 260/326.11 S

OTHER PUBLICATIONS

Chem. Abst. Subject Reading, vol. 86, 1977, 4905cs.

*Primary Examiner*—Jane T. Fan
*Attorney, Agent, or Firm*—Edward McC. Roberts

[57] ABSTRACT

An indolinospiropyrane compound of the formula

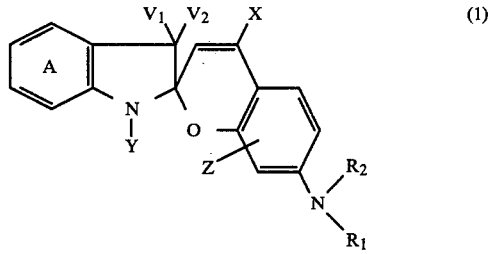

wherein
$R_1$ represents alkyl which has at most 12 carbon atoms and is unsubstituted or substituted by halogen, hydroxyl, cyano, lower alkoxy or lower alkyl-carbonyloxy, or cycloalkyl, phenyl or benzyl or phenyl or benzyl which are substituted by halogen, nitro, lower alkyl or lower alkoxy,
$R_2$ represents hydrogen, alkyl which has at most 12 carbon atoms and is unsubstituted or substituted by halogen, hydroxyl, cyano, lower alkoxy or lower alkyl-carbonyloxy, or cycloalkyl or benzyl which is unsubstituted or substituted by halogen, nitro, lower alkyl or lower alkoxy, or
$R_1$ and $R_2$, together with the nitrogen atom which links them, represent a 5-membered or 6-membered heterocyclic radical,
X represents alkyl which has at most 12 carbon atoms and is unsubstituted or substituted by halogen, unsubstituted or substituted benzyl or phenyl or an unsubstituted or substituted heterocyclic radical,
Y represents alkyl which has at most 12 carbon atoms and is unsubstituted or substituted by halogen, cyano or lower alkoxy, or benzyl which is unsubstituted or substituted by halogen, nitro, lower alkyl or lower alkoxy,
Z represents hydrogen, halogen or lower alkyl and
$V_1$ and $V_2$ each represent lower alkyl, cycloalkyl or benzyl, or conjointly represent alkylene, and
the ring A is unsubstituted or substituted by halogen, nitro, cyano, trifluoromethyl, lower alkyl, lower alkoxy, lower alkoxy-carbonyl, phenoxy, amino, lower alkylamino or N-lower alkyl-carbonylamino; these compounds are distinguished by an outstanding storage stability and are particularly useful as color formers which give intense orange, red or violet color shades of excellent light fastness when they are brought into contact with an electron-accepting co-reactant.

5 Claims, No Drawings

INDOLINOSPIROPYRANE COMPOUNDS

This is a division of application Ser. No. 109,741 filed on Jan. 4, 1980, which is a division of application Ser. No. 761,042, filed Jan. 21, 1977, now U.S. Pat. No. 4,210,591.

The present invention relates to new indolinospiropyrane compounds, processes for their manufacture and their use in pressure-sensitive or heat-sensitive recording materials.

The new indolinospiropyrane compounds correspond to the general formula

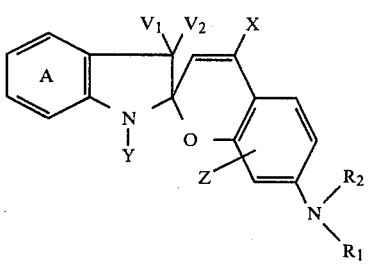

in which $R_1$ denotes alkyl which has at most 12 carbon atoms and is unsubstituted or substituted by halogen, hydroxyl, cyano, lower alkoxy or lower alkyl-carbonyloxy, or cycloalkyl, phenyl or benzyl or phenyl or benzyl which are substituted by halogen, nitro, lower alkyl or lower alkoxy, $R_2$ denotes hydrogen, alkyl which has at most 12 carbon atoms and is unsubstituted or substituted by halogen, hydroxyl, cyano, lower alkoxy or lower alkyl-carbonyloxy, or cycloalkyl or benzyl which is unsubstituted or substituted by halogen, nitro, lower alkyl or lower alkoxy, or $R_1$ and $R_2$, together with the nitrogen atom which links them, denote a 5-membered or 6-membered, preferably saturated, heterocyclic radical, X denotes alkyl which has at most 12 carbon atoms and is unsubstituted or substituted by halogen, unsubstituted or substituted benzyl or phenyl or an unsubstituted or substituted heterocyclic radical, Y denotes alkyl which has at most 12 carbon atoms and is unsubstituted or substituted by halogen, cyano or lower alkoxy, or benzyl which is unsubstituted or substituted by halogen, nitro, lower alkyl or lower alkoxy, Z denotes hydrogen, halogen or lower alkyl and $V_1$ and $V_2$ each denote lower alkyl, cycloalkyl or benzyl, or conjointly denote alkylene, and the ring A can be further substituted by halogen, nitro, cyano, trifluoromethyl, lower alkyl, lower alkoxy, lower alkoxy-carbonyl, phenoxy, amino, lower alkylamino or N-lower alkyl-carbonylamino. When benzyl is substituted, it is understood that it is substituted on the aromatic nucleus thereof.

Amongst the compounds of the formula (1), those in which X denotes alkyl which has at most 12 carbon atoms and is unsubstituted or substituted by halogen, or benzyl, phenyl or benzyl or phenyl which are substituted by halogen, nitro, lower alkyl, lower alkoxy or the amino group

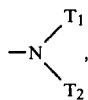

in which $T_1$ and $T_2$ independently of one another represent hydrogen, lower alkyl or lower alkyl-carbonyl, or $T_1$ and $T_2$, together with the nitrogen atom which links them, represent a 5-membered or 6-membered heterocyclic radical, are preferred.

In the definition of the radicals of the spiropyrane compounds, lower alkyl and lower alkoxy as a rule represent those groups or constituents of groups which contain 1 to 5, and especially 1 to 3, carbon atoms, such as, for example, methyl, ethyl, n-propyl, isopropyl, n-butyl, sec.-butyl or amyl and, respectively, methoxy, ethoxy or isopropoxy.

If the substituents $R_1$, $R_2$, X and Y represent alkyl groups, they can be straight-chain or branched alkyl radicals. Examples of such alkyl radicals are methyl, ethyl, n-propyl, isopropyl, n-butyl, sec.-butyl, n-hexyl, n-octyl or n-dodecyl.

If the alkyl radicals in $R_1$, $R_2$, X and Y are substituted, they are, in accordance with the indicated substitution, above all cyanoalkyl, halogenoalkyl, hydroxyalkyl or alkoxyalkyl, in each case with 2 to 4 carbon atoms, such as, for example, $\beta$-cyanoethyl, $\beta$-chloroethyl, $\beta$-hydroxyethyl, $\beta$-methoxyethyl or $\beta$-ethoxyethyl. If the alkyl groups in $R_1$ and $R_2$ contain a lower alkyl-carbonyloxy group, the latter is, for example, an acetyloxy group or propionyloxy group.

Examples of cycloalkyl in the meaning of the R and V radicals are cyclopentyl or, preferably, cyclohexyl.

Examples of preferred substituents in the benzyl group of the R, X and Y radicals and in the phenyl group of $R_1$ and X are halogens, nitro, methyl or methoxy. Examples of such araliphatic and aromatic radicals are o- or p-methylbenzyl, o- or p-chlorobenzyl, o- or p-nitrobenzyl, o- or p-tolyl, xylyl, o-, m- or p-chlorophenyl, o- or p-nitrophenyl and o- or p-methoxyphenyl.

The phenyl radical in X can advantageously also contain an amino group, which can be monosubstituted or, preferably, disubstituted, especially by lower alkyl, such as, for example, methyl or ethyl, or benzyl. Examples of amino-substituted phenyl radicals X which may be mentioned are, in particular, p-dimethylaminophenyl, p-diethylaminophenyl and p-dibenzylaminophenyl.

If the pairs of substituents $R_1$ and $R_2$, and $T_1$ and $T_2$, in each case, together with the common nitrogen atom, represent a heterocyclic radical, the latter is, for example, pyrrolidino, piperidino, pipecolino, morpholino, thiomorpholino or piperazino.

As a heterocyclic radical, X above all represents a 5-membered or 6-membered heterocyclic structure of aromatic character which preferably contains oxygen, sulphur or nitrogen. Examples of such heterocyclic structures are thienyl, furyl, pyrrolyl, pyrazolyl, imidazolyl or pyridyl radicals. X can also represent a multinuclear heterocyclic ring system. This preferably contains a fused benzene or naphthalene ring, such as, for example, an optionally substituted benzothiophene, indolyl, benzothiazolyl, coumarin, quinoline or carbazolyl radical. The mononuclear or polynuclear heterocyclic radicals can be substituted, especially by halogen, hydroxyl, cyano, nitro, lower alkyl, lower alkoxy or lower alkoxycarbonyl. The preferred heterocyclic radicals in the meaning of X are 2-furyl, 2-thienyl, 2-, 3- or 4-pyridyl or 5-lower alkoxycarbonyl-2-thienyl, such as, for example, 5-carbomethoxy-2-thienyl.

The substituents $R_1$ and $R_2$ are preferably benzyl or lower alkyl. The N-substituent Y is, in particular, benzyl or alkyl with 1 to 8 carbon atoms, for example n- octyl or, above all, methyl or ethyl. Z is preferably hydrogen. X is preferably lower alkyl, benzyl, phenyl or phenyl substituted by halogen, nitro, methyl, methoxy or lower alkylamino.

The radicals $V_1$ and $V_2$ can differ from one another or are preferably identical.

$V_1$ and $V_2$ preferably denote lower alkyl and above all both denote methyl. If $V_1$ and $V_2$ conjointly denote alkylene, they advantageously contain 4 or 5 carbon atoms and form, together with the carbon atom which links them, a cyclopentane or cyclohexane ring.

The ring A is preferably not further substituted or is further substituted by halogen, lower alkyl, lower alkoxy or lower alkoxy-carbonyl, for example by chlorine, methyl, methoxy or carbomethoxy.

Colour-forming agents comprising spiropyrane compounds of the formula (1) which are important in practice correspond to the general formula

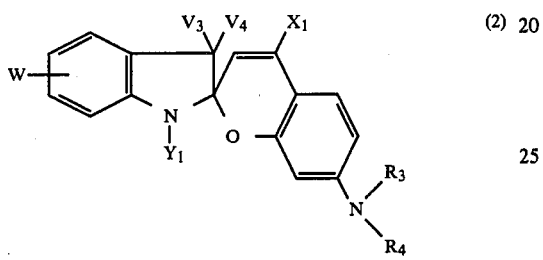
(2)

in which $R_3$ and $R_4$ independently of one another denote lower alkyl which is unsubstituted or substituted by halogen, cyano, lower alkoxy or lower alkyl-carbonyloxy, or benzyl, or $R_3$ and $R_4$, together with the nitrogen atom which links them, denote a pyrrolidino, piperidino or morpholino radical, $X_1$ denotes lower alkyl, benzyl or phenyl which is unsubstituted or substituted by halogen, nitro, methyl, methoxy or lower alkylamino, $Y_1$ denotes alkyl with 1 to 8 carbon atoms or benzyl, $V_3$ and $V_4$ each denote lower alkyl, above all methyl, and W denotes hydrogen, halogen, lower alkyl, lower alkoxy or lower alkoxycarbonyl. W is preferably hydrogen.

In the context of the above substituents in formulae (1) and (2), halogen is, for example, fluorine, bromine or, preferably, chlorine.

Indolinospiropyrane compounds of the general formula

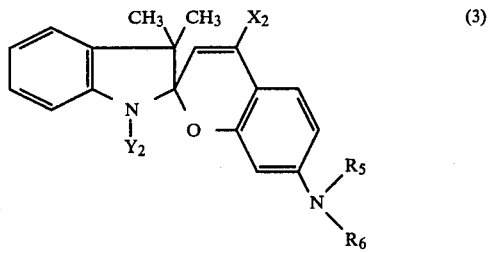
(3)

in which $R_5$ and $R_6$ independently of one another denote lower alkyl or benzyl, $X_2$ denotes lower alkyl, benzyl, phenyl, furyl, thienyl, lower alkoxycarbonylthienyl, pyridyl or phenyl which is substituted by nitro, chlorine, methyl, methoxy or lower alkylamino, and $Y_2$ denotes lower alkyl or benzyl are of very particular interest.

Compounds of the formula (3) in which $X_2$ represents methyl, ethyl, benzyl, phenyl or phenyl which is substituted by nitro, chloro, methyl, methoxy or lower alkylamino are of great interest in practice. Amongst these compounds of the formula (3), those in which $R_5$ and $R_6$ denote methyl or ethyl, $X_2$ denotes methyl, phenyl, p-nitrophenyl or p-diethylaminophenyl and $Y_2$ denotes methyl, ethyl or benzyl are particularly preferred.

The indolinospiropyrane compounds according to the invention are manufactured by reacting an indoline compound of the general formula

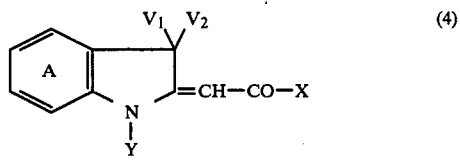
(4)

with a phenol compound of the general formula

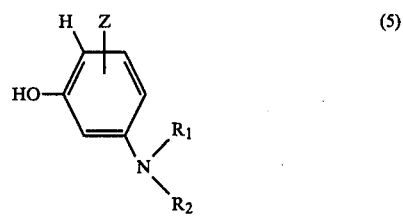
(5)

in which A, $V_1$, $V_2$, X, Y, Z, $R_1$ and $R_2$ have the indicated meanings.

The reaction is preferably carried out by reacting the reactants in the presence of an acid dehydrating agent. Examples of such condensing agents are acetic anhydride, sulphuric acid, oleum, zinc chloride or, preferably, acid halides.

Acid halides which can be used are acid bromides or, preferably, acid chlorides of phosphorous or sulphurous acid, of phosphoric acid, of sulphuric acid, of carbonic acid or of oxalic acid. Advantageously, oxalyl chloride, oxalyl bromide, thionyl chloride, sulphuryl chloride, phosphorus trichloride, phosphorus tribromide or, preferably, phosgene or, in particular, phosphorus oxychloride is used.

The reaction of the indoline compound of the formula (4) with the phenol compound of the formula (5) can be carried out at a temperature between $-10°$ and $+120°$ C. and preferably at between 20° and 100° C. It is advantageous to maintain anhydrous conditions. As excess of the acid halide can be used as the reaction medium but it is also possible to add a solvent which is inert under the reaction conditions.

Examples of solvents which can be used are: cycloaliphatic or aromatic hydrocarbons, such as, for example, cyclohexane, benzene, toluene or xylene; chlorinated hydrocarbons, such as chloroform, carbon tetrachloride, ethylene chloride or chlorobenzenes; and others, such as dioxane, diethyl ether, glycol dimethyl ether or tetrahydrofurane.

The concentration of the reactants is not critical; however, it is advantageous to use one mol equivalent of each of the reactants. As a rule, the manufacturing process is carried out by first allowing the indoline compound of the formula (4) and the acid halide to react and then adding the compound of the formula (5). However, it is also possible to mix all of the reactants, that is to say the compound of the formula (4), the compound of the formula (5) and the acid halide, at the same time. The end product of the formula (1) is isolated in a generally known manner, for example by pouring the reaction mixture into ice water, if necessary buffering the acids with an alkaline compound, for example alkali metal hydroxides or alkali metal carbonates, filtering off the precipitate formed and washing and drying and also, optionally, by recrystallising the product. Liquid end products can be obtained by extraction with suitable organic solvents and optionally purified by distillation.

As a rule, the starting materials of the formula (4) are obtained by reacting an indoline compound of the general formula

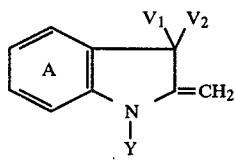
(6)

in which A, Y, $V_1$ and $V_2$ have the indicated meaning, with an acylating agent which introduces the radical X—CO—, especially a halide of the general formula (7) Hal—CO—X or an acid anhydride of the formula

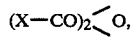

in which Hal denotes halogen and X has the indicated meaning, and the reaction is advantageously carried out in the presence of an acid-binding agent, for example alkali metal carbonates or alkali metal bicarbonates or tertiary nitrogen bases, such as pyridine.

The indolinospiropyrane compounds of the formulae (1) to (3) are usually colourless or at most slightly coloured. When these colour-forming agents are brought into contact with an acid developer, that is to say an electron acceptor, they give intense orange, red or violet colour shades, which are outstanding fast to light. They are therefore also very valuable as a mixture with other known colour-forming agents, for example crystal violet lactone, 3,3-(bis-aminophenyl)phthalides, 2,6-diaminofluoranes or benzoylleucomethylene blue, in order to give blue, navy-blue, grey or black colourations. By virtue of the novel introduction of the substituent X into the spiropyrane nucleus, the colour-forming agents according to the invention are surprisingly distinguished by an outstanding storage stability, which is of great practical importance, especially for use in microcapsules.

The new colour-forming agents are above all suitable for use in a pressure-sensitive or heat-sensitive recording material, which can be copying material and also documenting material.

A pressure-sensitive material comprises, for example, at least one pair of sheets which contain at least one colour-forming agent of the formulae (1) to (3), dissolved in an organic solvent, and an electron acceptor substance as the developer. The colour-forming agent gives a coloured marking at the points at which it comes into contact with the electron acceptor substance.

Typical examples of such developers are attapulgite clay, silton clay, silicon dioxide, bentonite, halloysite, aluminium oxide, aluminium sulphate, aluminium phosphate, zinc chloride, kaolin or any other desired clay or organic compounds having an acid reaction, such as, for example, optionally ring-substituted phenols, salicylic acid or salicylates and their metals salts, and also a polymeric material having an acid reaction, such as, for example, a phenolic polymer, an alkylphenolacetylene resin, a maleic acid/rosin resin or a partially or completely hydrolysed polymer of maleic anhydride with styrene, ethylene, vinyl methyl ether or carboxymethylene. Attapulgite clay, silton clay or a phenol-formaldehyde resin are preferred developers. These electron acceptors are preferably applied in the form of a layer to the front of the receiving sheet.

In order to prevent the colour-forming agents, which are contained in the pressure-sensitive recording material, from becoming prematurely active, they are as a rule separated from the electron acceptor substance. This can appropriately be achieved by incorporating the colour-forming agents into foam-like, sponge-like or honeycombed structures. Preferably, however, the colour-forming agents are enclosed in microcapsules, which can as a rule be crushed by pressure.

When the capsules are crushed by pressure, for example by means of a pencil, and when the solution of the colour-forming agent is transferred in this way onto an adjacent sheet which is coated with an electron acceptor, a coloured area is produced. This colour results from the dyestuff, formed during this process, which absorbs in the visible region of the electromagnetic spectrum.

The colour-forming agents are preferably encapsulated in the form of solutions in organic solvents. Examples of suitable solvents are preferably non-volatile solvents, for example polyhalogenated diphenyl, such as trichlorodiphenyl, or a mixture thereof with liquid paraffin, and also tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of diphenyl, naphthalene or triphenyl, terphenyls, partially hydrogenated terphenyl or other chlorinated or hydrogenated, fused, aromatic hydrocarbons.

The capsule walls can be formed uniformly around the droplets of the solution of the colour-forming agent by means of coaservation forces, and the encapsulated material can consist, for example, of gelatine and gum arabic, as described, for example, in U.S. Pat. No. 2,800,457. The capsules can preferably also be formed from an aminoplast or modified aminoplasts by polycondensation, as described in British Pat. Nos. 989,264 and 1,156,725.

The microcapsules containing the colour-forming agents of the formula (1) can be used for the manufacture of pressure-sensitive copying materials of the most diverse known types. The various systems differ from one another essentially in the arrangement of the capsules and of the colour reactants and in the carrier material.

A preferred arrangement is that in which the encapsulated colour-forming agent is applied in the form of a layer to the back of a transfer sheet and the electron acceptor substance is applied in the form of a layer to the front of a receiving sheet. However, the components can also be used in the paper pulp.

Another arrangement of the components is for the microcapsules containing the colour-forming agent and the developer to be in or on the same sheet, in the form of one or more individual layers, or in the paper pulp.

Such pressure-sensitive copying materials are described, for example, in U.S. Pat. Nos. 2,730,457, 2,932,582, 3,418,250, 3,418,656, 3,427,180 and 3,516,846. Further systems are described in British Pat. Nos. 1,042,596, 1,042,597, 1,042,598, 1,042,599, 1,053,935 and 1,517,650. Microcapsules which contain the colour-forming agents of the formula (1) are suitable for each of these systems and also for other pressure-sensitive systems.

The capsules are preferably secured to the carrier by means of a suitable adhesive. Since paper is the preferred carrier material, these adhesives are in the main paper-coating agents, such as gum arabic, polyvinyl alcohol, hydroxymethylcellulose, casein, methylcellulose or dextrin.

The term "paper" used here includes not only normal papers of cellulose fibres but also papers in which the cellulose fibres are replaced (partially or completely) by fibres of synthetic polymers.

The indolinospiropyrane compounds of the formulae (1) to (3) can also be used as colour-forming agents in a thermo-reactive recording material. This recording material as a rule contains at least one carrier, a colour-forming agent, an electron acceptor substance and, if appropriate, also a binder. Thermo-reactive recording systems include, for example, heat-sensitive recording and copying materials and papers. These systems are used, for example, for recording information, for example in computers, teleprinters or telex machines, or in measuring instruments. The production of the image (production of the marking) can also be effected manually with a heated pen. Laser beams are a further device for producing markings by means of heat.

The thermo-reactive recording material can be built up in such a way that the colour-forming agent is dissolved or dispersed in a layer of binder and the developer is dissolved or dispersed in the binder in a second layer. Another possibility is for both the colour-forming agent and the developer to be dispersed in one layer. The binder is softened by means of heat in specific areas and at these points, at which heat is applied, the colour-forming agent comes into contact with the electron acceptor substance and the desired colour develops immediately.

The developers are the same electron acceptor substances as are used in pressure-sensitive papers. Examples of developer are the clay minerals and phenolic resins already mentioned, or phenolic compounds, such as, for example, 4-tert.-butylphenol, 4-phenylphenol, 4-hydroxydiphenyl ether, α-naphthol, β-naphthol, methyl 4-hydroxybenzoate, 4-hydroxyacetophenone, 2,2′-dihydroxydiphenyl, 4,4′-isopropylidenediphenol, 4,4′-isopropylidene-bis-(2-methylphenol), 4,4′-bis-(hydroxyphenyl)-valeric acid, hydroquinone, pyrogallol, phloroglucinol, p-, m- and o-hydroxybenzoic acid, gallic acid, 1-hydroxy-2-naphthoic acid and also boric acid and aliphatic dicarboxylic acids, such as, for example, tartaric acid, oxalic acid, maleic acid, citric acid, citraconic acid or succinic acid.

Film-forming binders which can be melted are preferably used to manufacture the thermo-reactive recording material. These binders are usually soluble in water, whilst the spiropyrane compounds and the developer are insoluble in water. The binder should be capable of dispersing and fixing the colour-forming agent and the developer at room temperature.

The binder softens or melts under the action of heat, so that the colour-forming agent comes into contact with the developer and can form a colour. Examples of binders which are soluble in water or at least swellable in water are hydrophilic polymers, such as polyvinyl alcohol, polyacrylic acid, hydroxyethylcellulose, methylcellulose, carboxymethylcellulose, polyacrylamide, polyvinylpyrrolidone, gelatine and starch.

When the colour-forming agent and the developer are present in two separate layers, binders which are insoluble in water, that is to say binders which are soluble in non-polar or only slightly polar solvents, such as, for example, natural rubber, synthetic rubber, chlorinated rubber, alkyd resins, polystyrene, styrene/butadiene copolymers, polymethyl methacrylates, ethylcellulose, nitrocellulose and polyvinylcarbazole, can be used. However, the preferred arrangement is that in which the colour-forming agent and the developer are contained in a water-soluble binder in one layer.

The thermo-reactive layers can contain further additives. In order to improve the whiteness, to facilitate printing of the papers and to prevent the heated pen from adhereing, these layers can contain, for example, talc, $TiO_2$, $ZnO$ or $CaCO_3$, or also organic pigments, such as, for example, urea-formaldehyde polymers. In order to ensure that the colour is formed only within a limited temperature range, substances such as urea, thiourea, acetanilide, phthalic anhydride or other corresponding fusable products which induce simultaneous melting of the colour-forming agent and the developer, can be added.

In the examples which follow, the percentages quoted relate to weight, unless otherwise indicated.

EXAMPLE 1

21 g of 1,3,3-trimethyl-2-phenacylideneindoline are dissolved in 125 g of ethylene chloride and the solution is cooled to 0° C. 23 g of phosphorus oxychloride are then allowed to run in dropwise in the course of half an hour, at 0°–5° C., whilst stirring. 16.4 g of 3-diethylaminophenol are then added in portions to this solution. The reaction mixture is then warmed to 60° C., whilst stirring, and kept at this temperature for 6 hours, whilst stirring continuously. After the condensation reaction, the reaction solution is allowed to cool to room temperature and is poured into 300 g of ice water and the mixture is neutralised with a 10% strength solution of sodium hydroxide, whereupon two phases form. The organic phase is separated off, washed with water and dried over sodium sulphate. After purifying with active charcoal, it is evaporated. The residue is then dissolved in a little acetone and the solution is left to stand.

After some time, 21.8 g of an indolinospiropyrane compound of the formula

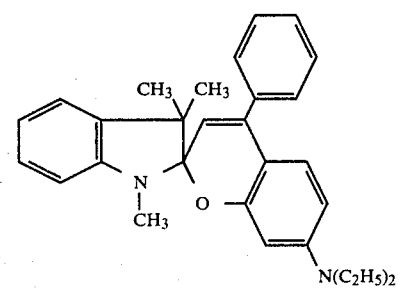

(11)

are isolated as colourless crystals. This compound melts at 141°–142° C.

Analysis: $C_{29}H_{32}N_2O$: Calculated: C, 82.0; H, 7.6; N, 6.6%. Found: C, 82.0; H, 7.7; N, 6.6%.

On silton clay, this colour-forming agent immediately forms a red-violet colouration.

EXAMPLE 2

8 g of 1,3,3-trimethyl-2-(p-nitro-phenacylidene)-indoline are dissolved in 100 g of ethylene chloride and the solution is cooled to 0° C. This is followed, at 0°–5° C., first by the dropwise addition of 8 g of phosphorus oxychloride and then by the addition of 4.2 g of 3-diethylaminophenol in portions. The reaction mixture is stirred for one hour at room temperature and then warmed to 80° C. and kept at this temperature for 3 hours. After the condensation reaction, the reaction solution is cooled and worked up as described in Example 1. After recrystallisation from ethanol/water, 4.1 g of an indolinospiropyrane compound of the formula

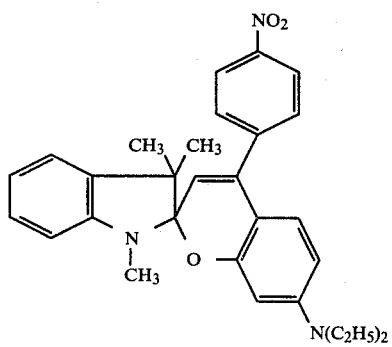
(12)

are obtained as yellow crystals. The melting point of this compound is 224°–225° C.

Analysis: $C_{29}H_{31}N_3O_3$: Calculated: C, 74.2; H, 6.6; N, 8.9%. Found: C, 73.9; H, 6.6; N, 8.9%.

On silton clay, this colour-forming agent immediately forms a violet colouration.

EXAMPLE 3

7.0 g of 1,3,3-trimethyl-2-(p-N,N-diethylaminophenacylidene)-indoline and 5 g of 3-diethylaminophenol are dissolved in 65 g of ethylene chloride and the solution is cooled to 0° C. 5 g of phosphorus oxychloride are then added dropwise. The reaction mixture is warmed to 60° C. and kept at this temperature for 5 hours. After the reaction, the reaction solution is cooled and worked up as described in Example 1. Recrystallisation from ethanol/water gives 2.5 g of an indolinospiropyrane compound of the formula

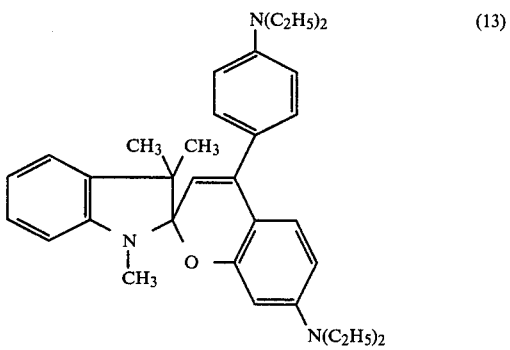
(13)

as white crystals. The melting point of this compound is 163°–165° C.

Analysis: $C_{33}H_{41}N_3O$: Calculated: C, 80.0; H, 8.2; N, 8.5%. Found: C, 79.0; H, 8.1; N, 8.4%.

On silton clay, this colour-forming agent immediately forms a red colouration.

EXAMPLE 4

5.4 g of 1,3,3-trimethyl-2-acetonylidene-indoline and 8.3 g of 3-diethylaminophenol are dissolved in 90 g of ethylene chloride and the solution is cooled to 0° C. 5.8 g of phosphorus oxychloride are allowed to run dropwise into this solution. The mixture is then allowed to react for 5 to 6 hours at room temperature. After the reaction, the reaction solution is worked up as described in Example 1. This gives 5.4 g of an indolinospiropyrane compound of the formula

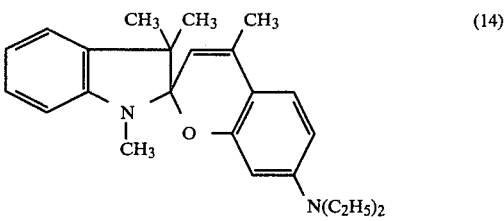
(14)

as colourless crystals. The melting point of this compound is 185°–187° C.

Analysis: $C_{24}H_{30}N_2O$: Calculated: C, 79.5; H, 8.2; N, 7.7%. Found: C, 79.4; H, 8.1; N, 7.6%.

On silton clay, this colour-forming agent immediately develops a red colouration.

EXAMPLE 5

22.9 g of 1,3,3-trimethyl-2-propionylidene-indoline and 24.8 g of 3-diethylaminophenol are dissolved in 50 g of ethylene chloride and the solution is cooled to 0° C. 23.0 g of phosphorus oxychloride are allowed to run dropwise into this solution and the mixture is stirred for 15 hours at room temperature. The reaction solution is then worked up as described in Example 1. After recrystallisation from acetone/water, this gives 17.9 g of an indolinospiropyrane compound of the formula

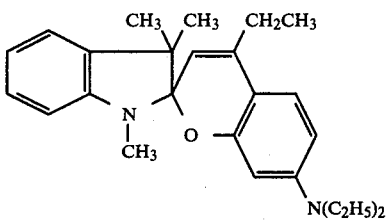

as colourless crystals. The melting point of this compound is 137°–138° C.

Analysis: $C_{25}H_{32}N_2O$: Calculated: C, 79.7; H, 8.6; N, 7.4%. Found: C, 79.7; H, 8.8; N, 7.2%.

On silton clay, this colour-forming agent immediately develops a red colouration.

EXAMPLE 6

12.2 g of 1,3,3-trimethyl-2-butyrylidene-indoline and 12.4 g of 3-diethylaminophenol are dissolved in 30 g of ethylene chloride and the solution is cooled to 0° C. 11.5 g of phosphorus oxychloride are allowed to run dropwise into this solution and the mixture is stirred for 15 hours at room temperature. The reaction solution is then worked up as described in Example 1. After recrystallisation from acetone/water, this gives 9.4 g of an indolinospiropyrane compound of the formula

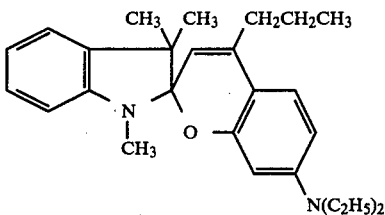

as colourless crystals. The melting point of this compound is 88°–90° C.

Analysis: $C_{26}H_{34}N_2O$: Calculated: C, 80.0; H, 8.8; N, 7.1%. Found: C, 80.2; H, 9.0; N, 7.0%.

On silton clay, this colour-forming agent immediately develops a red colouration.

EXAMPLE 7

14.6 g of 1,3,3-trimethyl-2-phenyl-acetylidene-indoline are dissolved in 80 g of ethylene chloride and the solution is cooled to 0° C. 13.1 g of phosphorus oxychloride are then allowed to run in dropwise at 0°–5° C., whilst stirring, and the mixture is stirred for 1 hour at 5° C. 12.4 g of 3-diethylaminophenol are then added in portions to this solution. The reaction mixture is stirred for 6 hours at room temperature and then worked up as described in Example 1.

After recrystallisation from acetone/water, this gives 10.5 g of an indolinospiropyrane compound of the formula

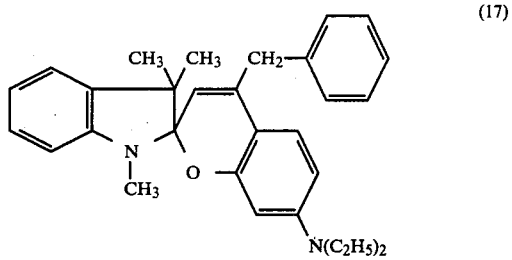

as colourless crystals. The melting point of this compound is 141°–143° C.

Analysis: $C_{30}H_{34}N_2O$: Calculated: C, 82.1; H, 7.8; N, 6.4%. Found: C, 81.5; H, 7.8; N, 6.3%.

On silton clay, this colour-forming agent immediately develops a red-violet colour.

EXAMPLE 8

7.8 g of 1,3,3-trimethyl-2-(p-chloro-phenacylidene)-indoline and 6.6 g of 3-diethylaminophenol are added in portions, at 0° C., to 100 g of phosphorus oxychloride. The reaction mixture is then stirred for 6 hours at room temperature. After the condensation reaction, the reaction solution is poured into 1,500 g of ice water and the mixture is rendered strongly alkaline with concentrated sodium hydroxide solution. The precipitate which has formed is filtered off. After recrystallisation from ethanol, this gives 9.0 g of an indolinospiropyrane compound of the formula

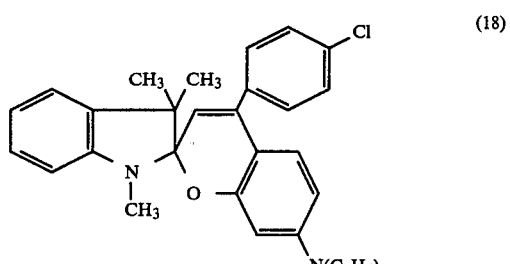

as colourless crystals. The melting point of the compound is 192°–194° C.

Analysis: $C_{29}H_{31}ClN_2O$: Calculated: C, 75.8; H, 6.8; N, 6.1; Cl, 7.7%. Found: C, 75.8; H, 6.9; N, 6.1; Cl, 7.9%.

On silton clay, this colour-forming agent immediately forms a red-violet colouration.

EXAMPLE 9

6.6 g of 1,3,3-trimethyl-2-(fur-2'-oylidene)-indoline and 6.6 g of 3-diethylaminophenol are added in portions, at 0° C., to 60 g of phosphorus oxychloride. The reaction mixture is then allowed to react for 15 hours at 30° C., whilst stirring. The reaction mixture is then cooled again to 0° C., a further 6.6 g of 3-diethylaminophenol are added and the mixture is stirred for a further 3 hours at 30° C. The reaction solution is then poured into 500 g of ice water and the mixture is rendered alkaline with concentrated sodium hydroxide solution. The precipitate which has formed is filtered off and recrystallised from ethanol/water. This gives 3.0 g of an indolinospiropyrane compound of the formula

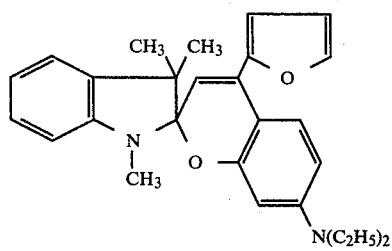

as colourless crystals. The melting point of this compound is 134°–135° C.

Analysis: $C_{27}H_{30}N_2O_2$: Calculated: C, 78.3; H, 7.3; N, 6.8%. Found: C, 78.4; H, 7.4; N, 6.9%.

On silton clay, this colour-forming agent immediately develops a greyish-tinged red colour.

EXAMPLE 10

5.0 g of 1,3,3-trimethyl-2-(5′-carbomethoxy-then-2′-oylidene)-indoline and 3.7 g of 3-diethylaminophenol are dissolved in 30 g of ethylene chloride and the solution is cooled to 0° C. 3.8 g of phosphorus oxychloride are then allowed to run in slowly dropwise and the reaction solution is then kept at 50° C. for 5 hours. The reaction solution is then again cooled to 0° C., a further 2.0 g of 3-diethylaminophenol and 2.0 g of phosphorus oxychloride are added and the mixture is stirred for 2 hours at 50° C. The reaction solution is then poured into 500 g of ice water and the mixture is rendered alkaline with concentrated sodium hydroxide solution and treated with chloroform. The chloroform solution is purified with animal charcoal and then evaporated. The residue is recrystallised from ethanol/water and gives 5.2 g of an indolinospiropyrane compound of the formula

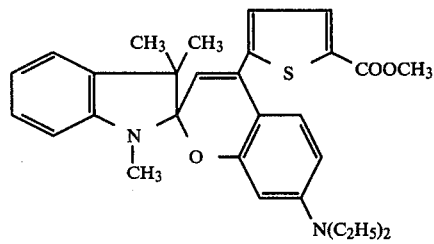

as pale yellowish crystals. The melting point of the compound is 188°–189° C.

Analysis: $C_{29}H_{32}N_2O_3S$: Calculated: C, 71.4; H, 6.6; N, 5.8%. Found: C, 71.2; H, 6.7; N, 5.8%.

On silton clay, this colour-forming agent immediately develops a reddish-tinged grey colour.

EXAMPLE 11

4.6 g of 1,3,3-trimethyl-2-(p-methoxyphenacylidene)indoline and 3.7 g of 3-diethylaminophenol are dissolved in 30 g of ethylene chloride and the solution is cooled to 0° C. 3.8 g of phosphorus oxychloride are then added. The reaction mixture is then stirred at 50° C. for 3 hours. After the condensation reaction, the reaction solution is cooled and worked up as described in Example 1.

Recrystallisation from ethanol gives 3.5 g of an indolinospiropyrane compound of the formula

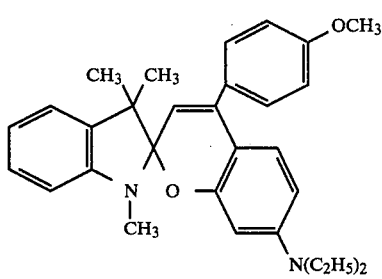

as colourless crystals. The melting point of this compound is 140°–142° C.

Analysis: $C_{30}H_{34}N_2O_2$: Calculated: C, 79.3; H, 7.6; N, 6.2%. Found: C, 79.6; H, 7.7; N, 6.3%.

On silton clay, this colour-forming agent immediately forms a red-violet colouration.

EXAMPLE 12

5.8 g of 1,3,3-trimethyl-2-(p-methylphenacylidene)indoline and 5.0 g of 3-diethylaminophenol are dissolved in 25 ml of ethylene chloride and the solution is cooled to 0° C. 5.0 g of phosphorus oxychloride are allowed to run dropwise into this solution. The mixture is then allowed to react at 40°–50° C. for 2 hours. After the reaction, the solution is worked up as described in Example 1.

After recrystallisation from acetone/ethanol, this gives 5.2 g of an indolinospiropyrane compound of the formula

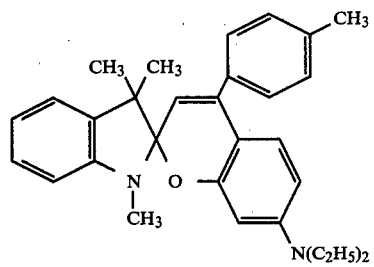

as colourless crystals. The melting point of this compound is 167°–170° C.

Analysis: $C_{30}H_{34}N_2O$: Calculated: C, 82.2; H, 7.8; N, 6.4%. Found: C, 82.3; H, 8.0; N, 6.3%.

On silton clay, this colour-forming agent immediately develops a red colouration.

EXAMPLE 13

5.8 g of 1,3,3-trimethyl-2-(p-methylphenacylidene)indoline and 8.7 g of 3-dibenzylaminophenol are dissolved in 30 g of ethylene chloride and the solution is cooled to 0° C. 5.0 g of phosphorus oxychloride are allowed to run dropwise into this solution and the mixture is then stirred for 4 hours at 50° C. After the reaction, the solution is worked up as described in Example 1.

After recrystallisation from ethanol, this gives 5.3 g of the indolinospiropyrane compound of the formula

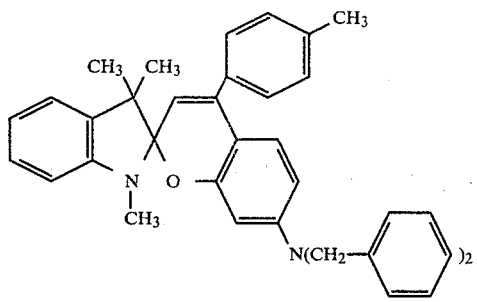

(23)

as colourless crystals. The melting point of this compound is 155°–160° C.

Analysis: $C_{40}H_{38}N_2O$: Calculated: C, 85.4; H, 6.8; N, 5.0%. Found: C, 84.9; H, 6.7; N, 4.9%.

On silton clay, this colour-forming agent immediately develops an orange-red colouration.

EXAMPLE 14

8.7 g of 1-benzyl-3,3-dimethyl-2-phenacylidene-indoline and 6.1 g of 3-diethylaminophenol are dissolved in 40 g of ethylene chloride and the solution is cooled to 0° C. 6.2 g of phosphorus oxychloride are allowed to run dropwise into this solution. The mixture is then stirred at 45° C. for 5 hours. After the reaction, the solution is worked up as described in Example 1.

After recrystallisation from ethanol, this gives 2.2 g of the indolinospiropyrane compound of the formula

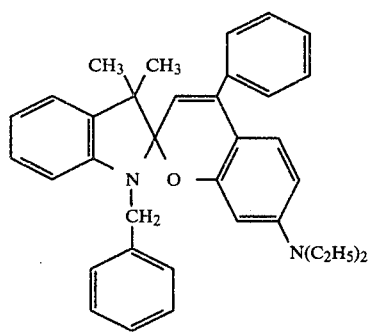

(24)

as colourless crystals. The melting point of this compound is 92°–95° C.

Analysis: $C_{35}H_{36}N_2O$: Calculated: C, 84.0; H, 7.2; N, 5.6%. Found: C, 85.0; H, 7.2; N, 5.5%.

On silton clay, this colour-forming agent immediately develops a red-violet colouration.

EXAMPLE 15

2.8 g of 1,3,3-trimethyl-2-isonicotinoylidene-indoline of the formula

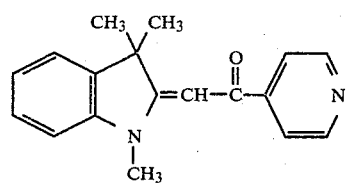

and 2.5 g of 3-diethylaminophenol are dissolved in 20 g of ethylene chloride and the solution is cooled to 0° C. 2.3 g of phosphorus oxychloride are allowed to run dropwise into this solution. The mixture is then stirred at 50° C. for 3 hours and left to stand at room temperature for 15 hours. After adding 1.5 g of 3-diethylaminophenol and 1.5 g of phosphorus oxychloride, the mixture is again warmed to 50° C. for 3 hours. After cooling, the solution is worked up as described in Example 1.

After recrystallisation from ethanol, this gives 1.6 g of the indolinospiropyrane compound of the formula

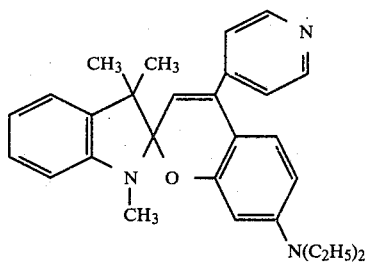

(25)

a colourless crystals. The melting point of the compound is 177°–179° C.

Analysis: $C_{28}H_{31}N_3O$: Calculated: C, 79.1; H, 7.3; N, 9.8%. Found: C, 79.0; H, 7.7; N, 9.5%.

On silton clay, the colour-forming agent immediately develops a red-violet colouration.

EXAMPLE 16

5.0 g of 1,3,3-trimethyl-5-chloro-2-acetonylideneindoline and 5.0 g of 3-diethylaminophenol are dissolved in 30 g of ethylene chloride and the solution is cooled to 0° C. 5.0 g of phosphorus oxychloride are then added dropwise. The reaction mixture is stirred at 45°–50° C. for 4 hours and then worked up as described in Example 1.

After recrystallisation from ethanol, this gives 2.2 g of an indolinospiropyrane compound of the formula (26)

as colourless crystals. The compound has a melting point of 179°–180° C.

Analysis: $C_{24}H_{29}ClN_2O$: Calculated: C, 72.6; H, 7.3; N, 7.1%. Found: C, 71.9; H, 7.4; N, 7.0%.

On silton clay, the colour-forming agent immediately develops a red-violet coloration.

EXAMPLE 17

Production of a pressure-sensitive copying paper

A solution of 3 g of the indolinospiropyrane compound of the formula (11) in 97 g of partially hydrogenated terphenyl is emulsified in a solution of 12 g of pigskin gelatine in 88 g of water at 50° C. A solution of 12 g of gum arabic in 88 g of water at 50° C. is then added and thereafter 200 ml of water at 50° C. are added. The resulting emulsion is poured into 600 g of ice water and the mixture is cooled and by this means coacervation is effected. A sheet of paper is coated with the suspension of microcapsules which is thus obtained, and dried. A second sheet of paper is coated with silton clay. The first sheet and the paper coated with silton clay are placed on top of one another with the coatings adjacent to one another.

Pressure is exerted by writing by hand or with a typewriter on the first sheet and a red-violet copy, which is outstandingly fast to light, develops on the sheet coated with clay.

Corresponding violet or red shade effects can be achieved by using each of the other colour-forming agents of the formulae (12) to (26) indicated in the Examples.

EXAMPLE 18

Production of a thermo-reactive paper 6 g of an aqueous dispersion which contains 1.57% of the indolinospiropyrane compound of the formula (13) and 6.7% of polyvinyl alcohol are mixed with 134 g of an aqueous dispersion which contains 14% of 4,4-isopropylidenediphenol, 8% of attapulgite clay and 6% of polyvinyl alcohol. This mixture is applied to a paper and dried. A red colour, which has outstanding fastness to light, is obtained by bringing the paper into contact with a heated ballpoint pen.

Similar results are obtained when any of the other colour-forming agents of the formulae (11), (12) and (14) to (26) indicated in the Examples is used.

I claim:

1. An indolinospiropyrane compound of the formula

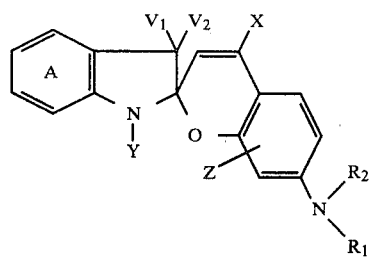

(1)

wherein $R_1$ represents alkyl which has at most 12 carbon atoms and is unsubstituted or substituted by halogen, hydroxyl, cyano, lower alkoxy or lower alkyl-carbonyloxy, or cyclopentyl or cyclohexyl, or phenyl or benzyl which are unsubstituted or substituted by halogen, nitro, lower alkyl or lower alkoxy, $R_2$ represents hydrogen, alkyl which has at most 12 carbon atoms and is unsubstituted or substituted by halogen, hydroxyl, cyano, lower alkoxy or lower alkyl-carbonyloxy, or cyclopentyl or cyclohexyl, or benzyl which is unsubstituted or substituted by halogen, nitro, lower alkyl or lower alkoxy, X represents a thienyl, furyl, pyrrolyl, pyridyl, benzothiophene, indolyl, quinolinyl or coumarin radical which is unsubstituted or substituted by halogen, hydroxyl, cyano, nitro, lower alkyl, lower alkoxy or lower alkoxy-carbonyl, Y represents alkyl which has at most 12 carbon atoms and is unsubstituted or substituted by halogen, cyano or lower alkoxy, or benzyl which is unsubstituted or substituted by halogen, nitro, lower alkyl or lower alkoxy, Z represents hydrogen, halogen or lower alkyl and $V_1$ and $V_2$ each represent lower alkyl, cyclopentyl, cyclohexyl or benzyl, or conjointly represent alkylene of 4 or 5 carbon atoms, and the ring A is unsubstituted or substituted by halogen, nitro, cyano, trifluoromethyl, lower alkyl, lower alkoxy, lower alkoxy-carbonyl, phenoxy, amino, lower alkylamino or N-lower alkyl-carbonylamino.

2. An indolinospiropyrane compound according to claim 1, wherein X is 2-furyl, 2-thienyl, 2-pyridyl, 3-pyridyl, 4-pyridyl or 5-lower alkoxycarbonyl-2-thienyl.

3. A compound according to claim 1 of the formula

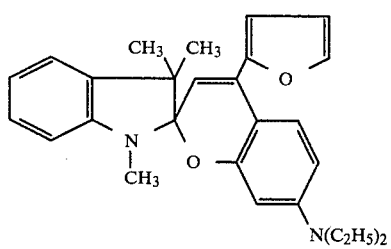

(19)

4. A compound according to claim 1 of the formula

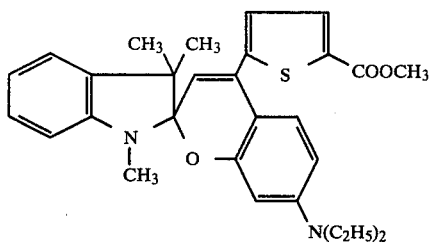

(20)

5. A compound according to claim 1 of the formula

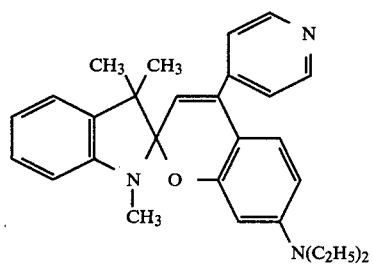

(25)

* * * * *